United States Patent [19]

Flynn et al.

[11] 4,412,448

[45] Nov. 1, 1983

[54] BLOCKING TEST FOR CHLORINATED POLYETHYLENE

[75] Inventors: James H. Flynn, Denham Springs; Donald E. McLemore, Baton Rouge, both of La.

[73] Assignee: The Dow Chemical Company, Midland, Mich.

[21] Appl. No.: 339,914

[22] Filed: Jan. 18, 1982

[51] Int. Cl.$^3$ ............................................. G01N 3/48
[52] U.S. Cl. ........................................ 73/81; 73/85; 73/821
[58] Field of Search .................. 73/821, 845, 823, 81, 73/85; 374/51, 53

[56] References Cited

U.S. PATENT DOCUMENTS 2,222,470  11/1940  Barnes .................................. 374/51

FOREIGN PATENT DOCUMENTS 387542  12/1923  Fed. Rep. of Germany .......... 73/81

OTHER PUBLICATIONS

Williams, J. C. et al., The Direct Measurement . . . Powder, From Powder Technology (Switzerland), vol. 4, No. 6, Sep. '71, pp. 328–337.

Primary Examiner—Jerry W. Myracle
Attorney, Agent, or Firm—A. J. Young

[57] ABSTRACT

A method is provided for measuring the tendency to and degree which a synthetic resinous particulate solid will block or agglomerate. The method comprises the steps of (a) forming a cake of a synthetic resinous particulate solid by compressing the particulate solid between substantially parallel surfaces at an elevated temperature, and (b) measuring the force required to break the cake by an elongated triangular-shaped wedge which is forced into the cake at a constant rate of speed.

10 Claims, 1 Drawing Figure

BLOCKING TEST FOR CHLORINATED POLYETHYLENE

BACKGROUND OF THE INVENTION

The present invention relates to a method for measuring the tendency of and degree which a synthetic resinous particulate solid will agglomerate. More particularly, the invention relates to a method for measuring the tendency and degree of chlorinated polyethylene particles to agglomerate.

"Blocking" is a term used to define the tendency of a polymeric resinous powder to form clumps or lumps by agglomeration. Blocking is generally undesirable because users of a resinous powder require that they remain free-flowing for storage, transport and blending purposes. A reliable test or method is therefore needed to measure and predict the tendency and degree of resinous powders such as chlorinated polyethylene (CPE) to block.

A prior-art method for measuring this tendency utilizes an instrument similar to that used to make column compression tests on structural materials, in which two flat plates are used to break a sample cake. This method can be used only for low-blocking synthetic resinous materials and, moreover, is inaccurate and unreliable.

SUMMARY

In general, the present invention provides a method for measuring the tendency of and degree which a synthetic resinous particulate solid will agglomerate, comprising the steps of (a) forming a cake of a synthetic resinous particulate solid by compressing the particulate solid between substantially parallel surfaces; and (b) measuring the force required to break the cake by an elongated triangular-shaped wedge which is forced into the cake at a constant rate of speed. The term "to agglomerate" is herein defined as meaning "to stick together and form larger particles by the combination of smaller particles."

It is an object of this invention to provide a method for determining the tendency and degree of a synthetic resinous particulate solid to agglomerate. It is a further object of the invention to provide a reliable method which is particularly beneficial for testing the tendency and degree of blocking for polymeric resins such as chlorinated polyethylene. Other objects of the invention will be apparent to those skilled in the art from the more detailed description which follows.

DESCRIPTION OF THE PREFERRED EMBODIMENT

Figure 1:
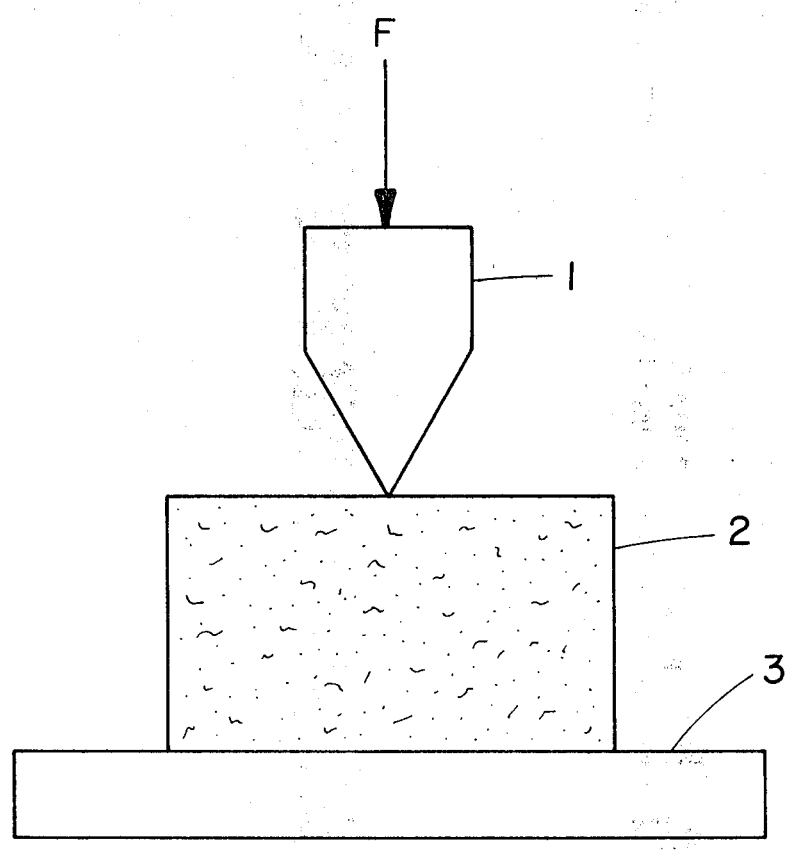

The following description illustrates the manner in which the principles of the present invention are applied, but is not to be construed as in any sense limiting the scope of the invention.

More specifically, the rate of speed at which the wedge penetrates the cake is beneficially controlled at about 3 inches or less per minute and, preferably, between about 0.1 and about 1 inch per minute. Most preferably, the wedge penetrates the cake at a rate of speed between about 0.4 and about 0.6 inch per minute.

The flat cake of synthetic resinous particulate solid is beneficially formed by compressing it at an elevated temperature. The temperature of compression depends on the type of material being tested. A temperature of between about 40° C. and about 70° C. has been found to be most beneficial for chlorinated polyethylene resins. The compression pressure is also maintained as desired for the material tested, and is beneficially between about ten pounds per square inch gauge and about twenty-five pounds per square inch gauge for chlorinated polyethylene resins. Preferably, the temperature is between about 48° C. and about 52° C., and the pressure between about seventeen pounds per square inch gauge and about twenty-one pounds per square inch gauge for chlorinated polyethylene resins. The compressed cake is cooled to a temperature of between about 20° C. and about 30° C. before measuring the force required to break the cake.

In carrying out the test method according to this invention, an Instron tester may be used to apply and measure the force on the cake. This device is described in ASTM Standard D 638 (1979), at pages 224 and 225, which is hereby incorporated by reference.

The apparatus includes a substantially flat plate on which a flat sample cake is placed, and a wedge that penetrates the cake at a fixed rate. The plate and wedge are clamped to the Instron tester, and the force required to break the cake is measured. Beneficially, the wedge includes an upper rectangular section and a lower wedge-shaped triangular section joined together. The leading edge of the elongated triangular section beneficially has a sharp V-shaped configuration at an angle of about 60 degrees but may be adjusted to any desired configuration or angle. Preferably, both ends of the wedge extend to at least about the opposite edges of the cake being tested.

The present invention will be further illustrated by means of the following example.

EXAMPLE 1

A two-inch diameter mold was filled with fifty grams of particulate chlorinated polyethylene resin. First and second polytetrafluoroethylene discs were positioned above and below the resin, respectively, to prevent sticking. The mold was placed in a 50° C. oven and the sample compressed for three hours under a pressure of nineteen pounds per square inch gauge. The mold was removed from the oven and allowed to cool to about 25° C. The cake was then removed from the mold and transferred to an Instron tester. A wedge as previously described herein was then lowered by the Instron tester to penetrate the cake. The rate of speed of the wedge in the Instron tester was preset to about one-half inch per minute. The force applied by the Instron tester was measured continuously as the wedge penetrated the cake up to the break-point of the resin cake. The force required to break the cake, which is the maximum force measured, provides a measure of the tendency to and degree which the chlorinated polyethylene resin tested will agglomerate. The breaking force required for twenty different tests of chlorinated polyethylene resin cakes are 20.9, 20.7, 19.2, 16.3, 19.7, 23.0, 21.5, 17.5, 19.1, 21.15, 18.9, 14.1, 19.5, 20.5, 16.8, 16.5, 20.2, 19.0, 17.3 with an average of 18.94. With the exception of one low reading, the narrow range of these tests clearly demonstrates the validity of this test method.

While certain representative embodiments and details have been shown for the purpose of illustrating the present invention, it will be apparent to those skilled in the art that various changes and modifications can be made therein without departing from the spirit and scope of the invention.

What is claimed is:

1. A method for measuring the tendency to and degree which a synthetic resinous particulate solid will agglomerate, comprising the steps of:
   (a) forming a cake of a synthetic resinous particulate solid by compressing the particulate solid between substantially parallel surfaces; and
   (b) measuring the force required to break the cake by an elongated triangular-shaped wedge which is forced into the cake at a constant rate of speed.

2. The method of claim 1, wherein the wedge penetrates the cake at a rate of speed of about three inches per minute or less.

3. The method of claim 2, wherein the wedge penetrates the cake at a rate of speed of between about 0.1 and about 1 inch per minute.

4. The method of claim 3, wherein the wedge penetrates the cake at a rate of speed of between about 0.4 and about 0.6 inch per minute.

5. The method of claim 1, wherein the cake is formed by compressing the particulate solid at a temperature of between about 40° C. and about 70° C.

6. The method of claim 5, wherein the cake is formed by compressing the particulate solid at a pressure between about ten pounds per square inch gauge and about twenty-five pounds per square inch gauge.

7. The method of claim 6, wherein the cake is formed by compressing the particulate solid at a pressure of between about seventeen pounds per square inch gauge and about twenty-one pounds per square inch gauge.

8. The method of claim 5, wherein the temperature is between about 48° C. and about 52° C.

9. The method of claim 8, wherein the pressure is between about ten pounds per square inch gauge and about twenty-five pounds per square inch gauge.

10. The method of claim 9, wherein the pressure is between about seventeen pounds per square inch gauge and about twenty-one pounds per square inch gauge.

* * * * *